United States Patent [19]
Artaki et al.

[11] Patent Number: 5,201,114
[45] Date of Patent: Apr. 13, 1993

[54] ANALYTIC METHOD FOR USE IN ELECTRONIC CIRCUIT ASSEMBLY OPERATIONS

[75] Inventors: Iris Artaki, Furlong, Pa.; Heidi M. Gordon, Willingboro; Urmi Ray, Plainsboro, both of N.J.

[73] Assignee: AT&T Bell Laboratories, Murray Hill, N.J.

[21] Appl. No.: 864,821

[22] Filed: Apr. 2, 1992

[51] Int. Cl.[5] .............................................. H05K 3/34
[52] U.S. Cl. .................. 29/840; 134/22.19; 210/902; 228/103; 361/400
[58] Field of Search ......................... 210/902, 908, 909; 134/13, 22.19; 228/103; 29/840; 361/400

[56] References Cited

U.S. PATENT DOCUMENTS 4,244,505  1/1981  Stokes, Jr. et al. ............. 228/103 X
4,244,506  1/1981  Stokes, Jr. et al. ............. 228/103 X

FOREIGN PATENT DOCUMENTS 3049364  3/1988  Japan .................................... 228/103

OTHER PUBLICATIONS

"Cleaning and Cleanliness Test Program Phase I Test Results", *Guidelines Report*, IPC, Lincolnwood, Ill., pp. 33–38.

"Modern Size-Exclusion Liquid Chromatography", W. W. Yaw et al., *John Wiley and Sons, Inc.*, 1979, pp. 381–449.

*Primary Examiner*—Carl J. Arbes
*Attorney, Agent, or Firm*—R. B. Anderson

[57] ABSTRACT

The accuracy of detection of the quantity of a rosin flux residue (18) left on an electronic assembly (11) after a cleaning operation is improved by using gel permeation chromatography for such detection.

9 Claims, 3 Drawing Sheets

ANALYTIC METHOD FOR USE IN ELECTRONIC CIRCUIT ASSEMBLY OPERATIONS

TECHNICAL FIELD

This invention relates to methods for assembling electronic circuit devices and, more particularly, to methods for monitoring the quantity of any rosin flux residue left on a circuit assembly after a cleaning operation.

BACKGROUND OF THE INVENTION

A key step in the assembly of electronic systems is the attachment and interconnection of electronic devices to bonding pads of a circuit pattern defined on a substrate which can be, for example, ceramic, silicon or FR-4 epoxy. In accordance with modern soldering techniques, solder elements are formed on the bonding pads of the substrate. A bonding pad array of the electronic device to be bonded to the substrate is contacted to the solder elements. A flux, such as rosin, is required for bonding. The assembly is then heated to a temperature sufficient to reflow or melt the solder to effect a bond between the arrays of bonding pads which, after the solder is hardened, constitutes both an electrical interconnection and a structural bond. The rosin flux is required to assure a dependable solder bond and, after the solder has been hardened, rosin flux residue is normally cleaned from the electronic assembly.

The most effective cleaning solvents for removing rosin flux residues are chlorofluorocarbon (CFC) based solvents. Because of their harmful effect on the environment, however, considerable work has been done to replace CFC solvents with more benign alternatives. Alternative solvents and alternative cleaning methods must of course be sufficiently effective in removing rosin residue that any remaining residue does not interfere with device performance. It has therefore become customary to specify a maximum quantity of rosin flux residue that is permitted to be left after a cleaning operation and to monitor certain electronic assemblies to determine that the allowed maximum has not been exceeded. If the monitoring shows that the maximum has been exceeded, then the cleaning operation is revised to make the cleaning more thorough.

As described, for example, in the paper, "Cleaning and Cleanliness Test Program Phase I Test Results," *Guidelines Report*, IPC, Lincolnwood, Ill., various methods that have been used for monitoring residue include Solid Insertion Probe Fourier Transform Mass Spectrometry (FTMS), Scanning Electron Microscope Electron Dispersive Spectrometry (SEM EDS), and Fourier Transform Infrared Spectrometry (FTIR). The method that is described as being generally preferred, however, is High Performance Liquid Chromatography (HPLC), which is deemed to be more practical for production line use.

Our work with HPLC has indicated that the method, as specified, significantly underestimates the quantity of rosin flux residue left on an electronic assembly after cleaning. Accordingly, there is still a need for better methods to assure that rosin flux residue has been properly cleaned, and specifically for quantitative methods for monitoring residue left after cleaning.

SUMMARY OF THE INVENTION

In accordance with the invention, the accuracy of detection of the quantity of rosin flux residue left on a patterned substrate after a cleaning operation is improved by using gel permeation chromatography for such detection.

These and other objects, features, and advantages of the invention will be better understood from a consideration of the following detailed description taken in conjunction with the accompanying drawing.

DETAILED DESCRIPTION

Figure 1:
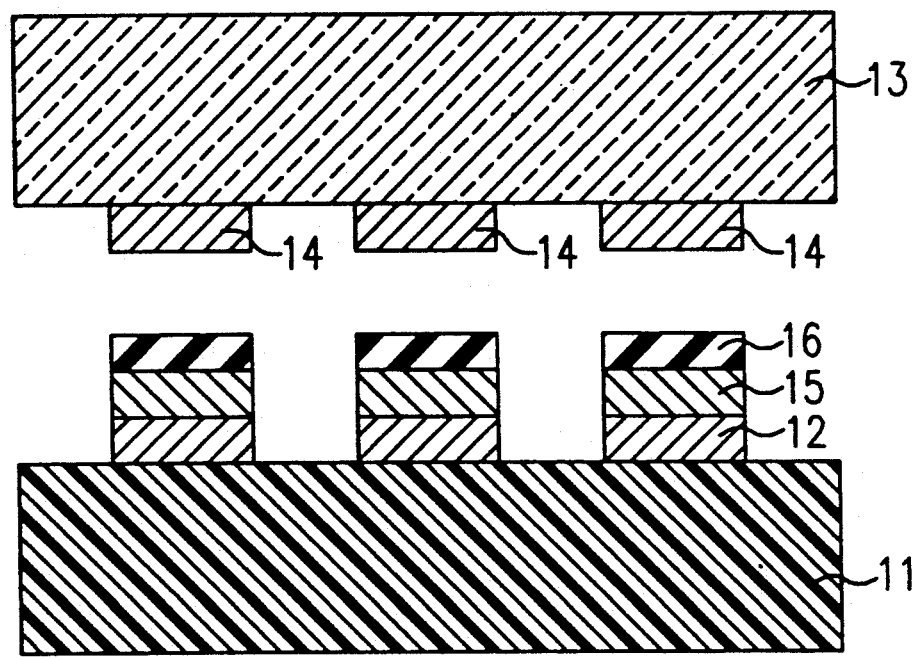
FIG. 1 is a schematic sectional view of part of a patterned substrate to which contacts of an electronic device are to be bonded.
Figure 2:
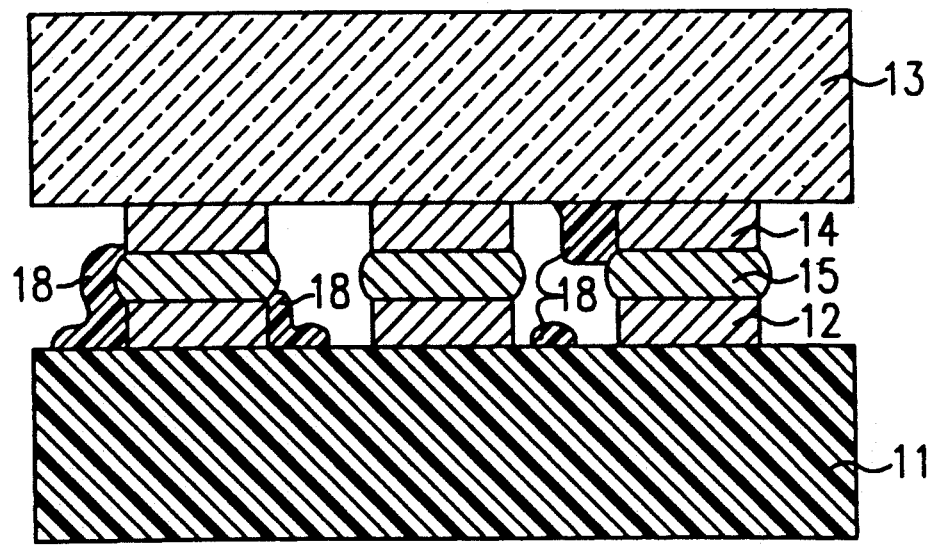
FIG. 2 is a schematic view of the apparatus of FIG. 1 at a subsequent stage of assembly.

It is to be noted that the drawings are schematic, are not necessarily to scale, and in some cases, the relative sizes of certain elements have been distorted for the purpose of clarity of exposition. Referring now to FIG. 1, there is shown a schematic view of a patterned substrate 11, which can be, for example, ceramic, silicon or FR-4 epoxy containing on an upper surface a conductive pattern including conductive bonding pads 12. It is desired to interconnect and bond an electronic device 13 to the substrate by attaching bonding pads 14 of the electronic device to matching bonding pads 12 of the substrate. As is known in the art, this can be accomplished by applying layers 15 of solder to bonding pads 12 and then applying a layer 16 of rosin flux over the solder layers 15. As shown in FIG. 2, the rosin flux 16 aids in the formation of a dependable solder bond between each matching pair of bonding pads.

The solder bonds are made by bringing the bonding pads 14 into contact with the solder layers 15 and then heating the assembly to reflow or to partially melt the solder layer. With the proper application of heat and pressure, the bonding pads 14 are reliably solder bonded to bonding pads 12 by way of solder interconnections which constitute both electrical conductors and structural elements of the final assembly. The soldering operation normally leaves solder flux residue 18 on the assembly which may be removed using any of a variety of known cleaning techniques.

Especially since the drive to replace CFC solvents with other cleaning materials, it has been recognized that the cleaning operation should be periodically monitored to make sure that residue left on the assembly after the cleaning operation is below some tolerable maximum. For example, each hundredth electronic assembly in a succession that are assembled and cleaned may be subjected to analysis to determine that the cleaning has been sufficiently thorough. Of course, particularly with increasing density of interconnections, it is important that residue not exceed a specified maximum to prevent possible malfunction due, for example, to static electronic effects and the like. If the maximum is exceeded, the cleaning operation is adjusted to make cleaning more thorough.

Figure 3:
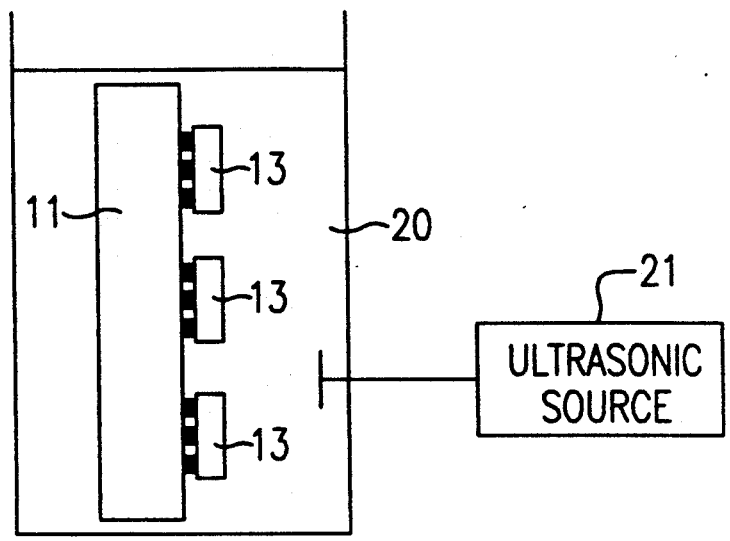
FIG. 3 is a schematic view of apparatus for extracting residue from an electronic assembly such as that shown in FIG. 2.

After cleaning, the first step in the analysis of residue is shown in FIG. 3 in which an electronic assembly comprising a patterned substrate 11 and a plurality of electronic devices 13 is placed within an ultrasonic bath containing a solvent 20. The solvent is excited by an ultrasonic source 21 that aids in the extraction of minute particles of rosin flux residue that may be left on the assembly after the cleaning operation. The solvent 20 is analyzed to determine the quantity of residue removed, thereby to determine whether the cleaning operation meets specifications. According to the prior art, solvent 20 is analyzed by processes such as High Performance Liquid Chromatography (HPLC), which we have determined to be significantly less reliable for such purposes than was previously thought to be the case.

We made our discovery by using gravimetric analysis to determine the amount of solder flux residue left on a ceramic substrate after a soldering operation. Gravimetric analysis requires the weighing of the substrate before and after the extraction operation and is not practical for routine production line monitoring. Further, it cannot be used with liquid absorbing substrates such as conventional printed wiring boards. Comparing the gravimetric analysis to the conventional HPLC analysis revealed that the HPLC method underestimated the quantity of rosin flux residue. Further study indicated that this was because of polymerization of the rosin flux during the solder bonding process which produced residue having molecular weights ranging from six hundred to one thousand or more. The conventional HPLC method is not well adapted to detect such molecules; in particular, it severely underestimates the quantity of such comparatively large molecules.

Figure 4:
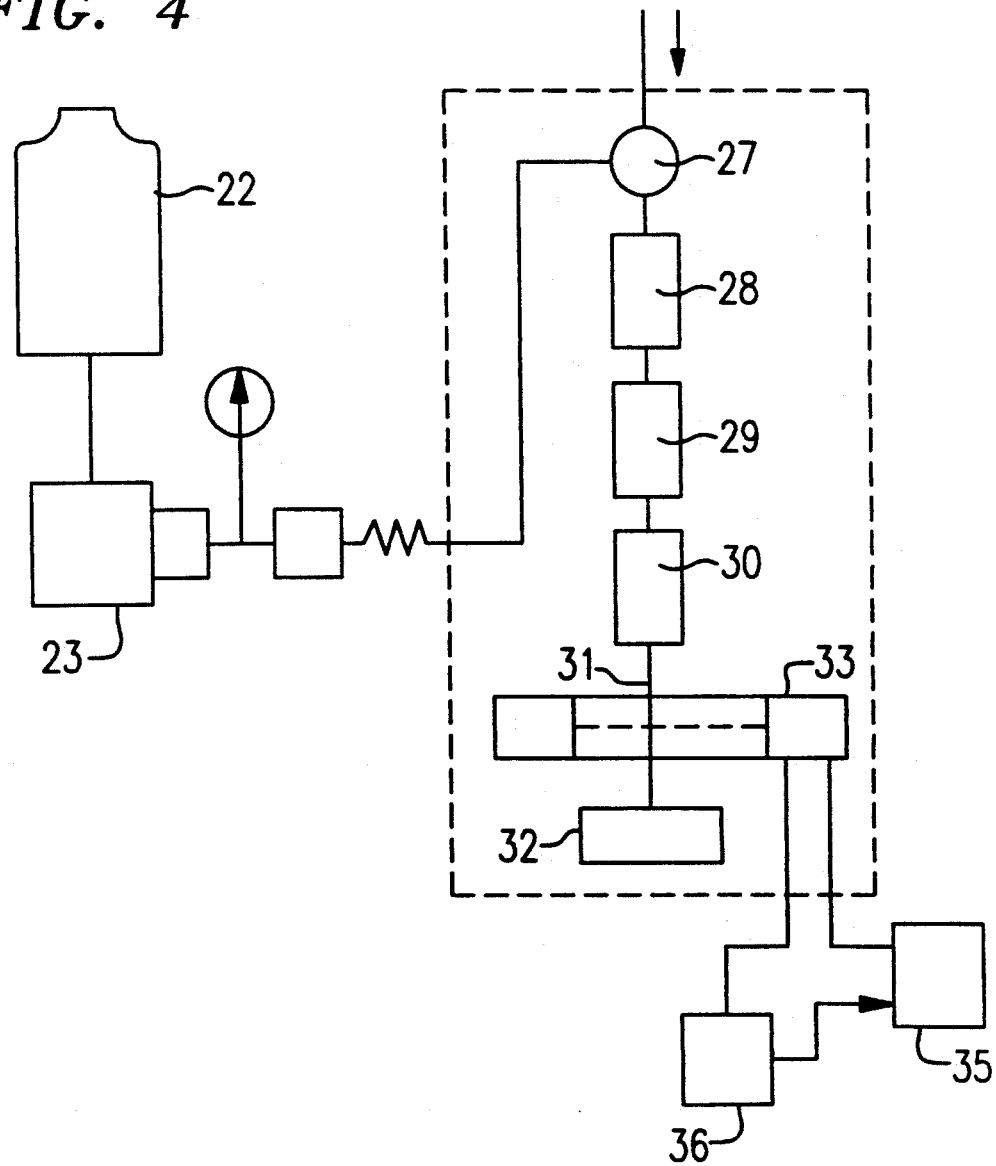
FIG. 4 is a schematic view of gel permeation chromatography apparatus used for analyzing residue-containing solvent taken from the apparatus of FIG. 3.

In accordance with the invention, the residue-containing solvent 20 of FIG. 3 is analyzed by the gel permeation chromatography (GPC) apparatus illustrated in FIG. 4. The solvent 20 or a dilution of the solvent is introduced into a sampling injector 27 as indicated by the arrow. The sampling injector mixes the solvent with a liquid from a reservoir 22; the liquid is referred to as the mobile phase or the carrier and may, for example, be liquid tetrahydrofuran. The mobile phase is pumped by a pump 23 and directed through a line filter to the sampling injector 27. The residue-containing solvent in the mobile phase is transmitted through successive GPC columns 28, 29, and 30, and a detector 33 to a collector reservoir 32. The output of the detector 33 is directed to a chromatograph recorder 35 and to data handling equipment 36.

Gel permeation chromatography is a known analytic procedure which is described, for example, in the book, "Modern Size-Exclusion Liquid Chromatography," W. W. Yaw, J. J. Kirkland, and D. D. Bly, John Wiley and Sons, Inc., 1979, hereby incorporated herein by reference, especially pp. 381–449. The solvent is directed through the three columns 28, 29, and 30, each of which contains a porous packing material such as highly cross-linked styrene divinylbenzene copolymer. The packing material of the different columns has different size pores; for example, the size of the pores in columns 28, 29, and 30 may be one hundred, five hundred, and one thousand angstroms, respectively. After transmission through the columns, an ultraviolet light is directed through the exiting material in detector 33. Detector 33 generates a signal indicative of light transmitted through the material exiting the column 30, and recorder 35 generates a chromatogram from the signal. Molecules that are too large to enter the packing pores move relatively quickly through the three columns and appear first in the chromatogram. Smaller molecules are retained by the column packing pores and move through the column at speeds dependent on their relative size, with the smallest molecules eluting last. Tetrahydrofuran may be used as the extracting solvent of FIG. 3 as well as the mobile phase that passes through the three columns.

In experiments that were conducted, the gel permeation chromatography apparatus shown in FIG. 4 was a "Waters 840 Data and Chromatography Control Station," available from the Millipore Corporation, Milford, Mass. A large number of chromatograms were obtained, such as that shown in FIG. 5 in which curve 37 represents an envelope of peaks recorded by the chromatograph. The ordinate measures the absorbance of light by the eluent which is proportional to the quantity of residue at a given time. The curve 37 therefore represents the quantity of residue detected having different molecular weights, the larger molecular weights being recorded first, at the lower retention times, with the higher retention times being indicative of lower molecular weights.

Figure 5:
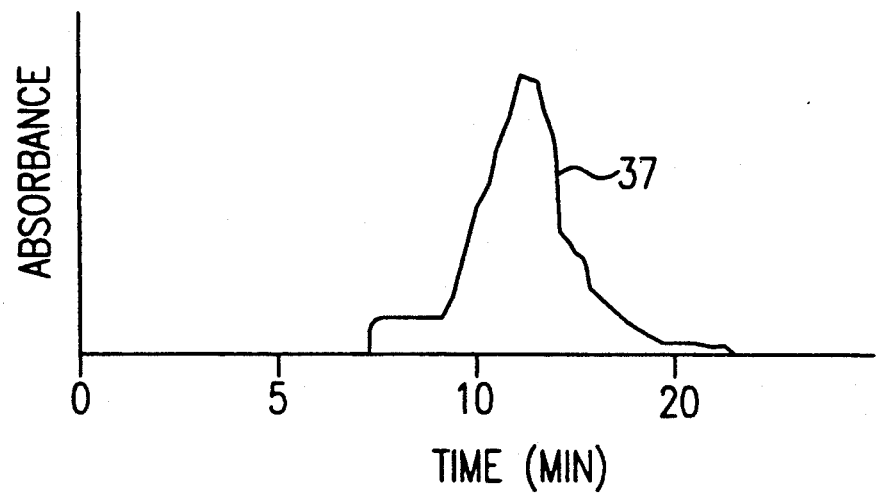
FIG. 5 is an example of a chromatograph of the type that can be made by the apparatus of FIG. 4.

The curve of FIG. 5 is useful, of course, only to the extent that it accurately reflects the quantity of residue contained on the electronic assembly of FIG. 3. We have established the correlation of the area under the GPC chromatogram with the rosin weight obtained by gravimetric methods, such correlation being illustrated in FIG. 6 by points 38. A series of standard rosin solutions varying in concentration from ten to four hundred parts per million were also prepared in tetrahydrofuran (weight by weight). The area under each of the GPC chromatograms for each of these standard samples was plotted as a function of rosin weight as shown by the points 39 in the graph of FIG. 6. The points all fall on the same straight line 37 which, for the experimental conditions used, fit the equation:

$$\text{Residue Weight (micrograms)} = (75 \times 10^{-6} \times \text{peak area}) \quad (1)$$

With the invention, this equation has a quality of fit value of 0.970 which indicates a high degree of calibration. GPC is normally used for the purpose of determining actual molecular weights. Standards were not used for the determination of the actual molecular weights of the polymerized rosin species because the quantity of interest here is the total amount of residue, rather than the distribution of the individual oligomers.

Figure 6:
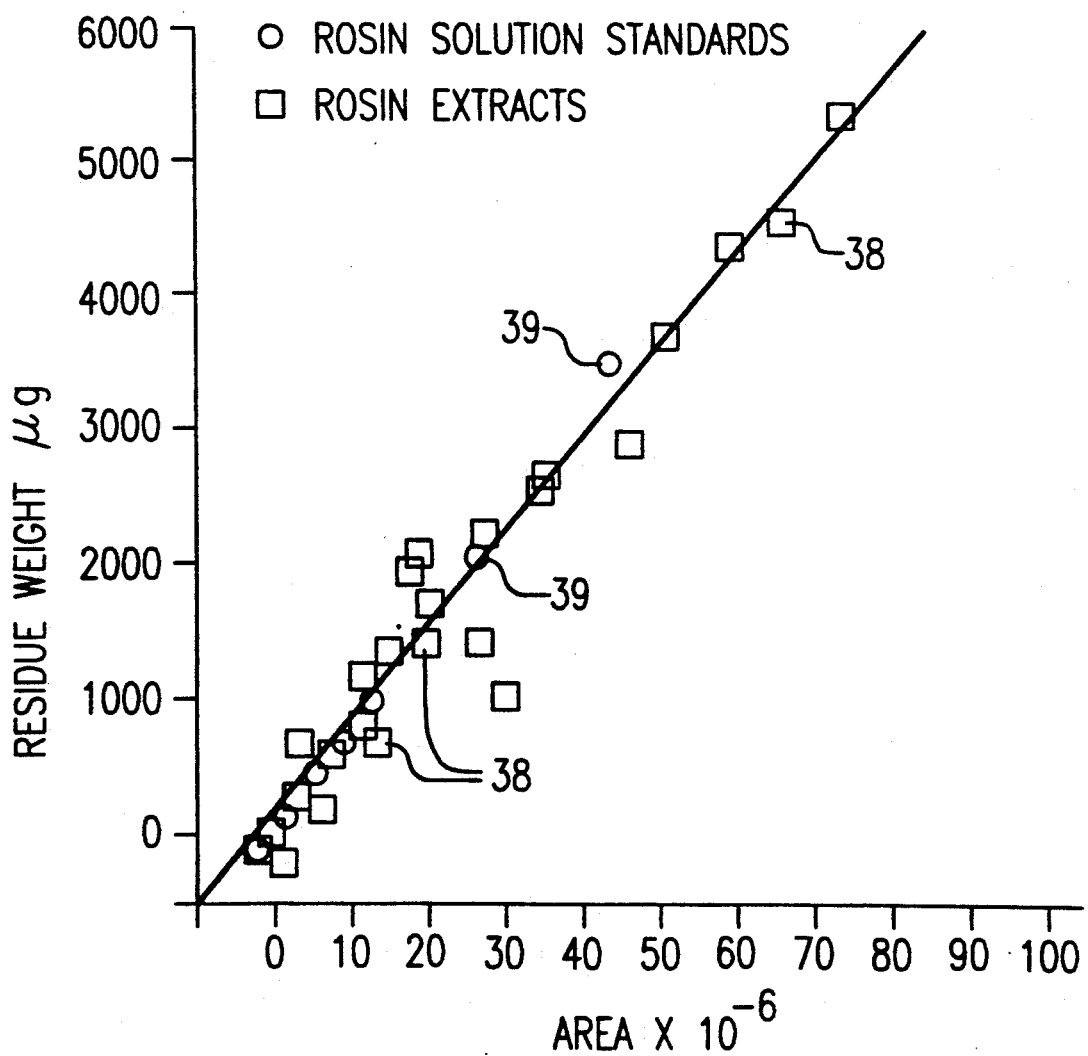
FIG. 6 is a graph showing the relationship of area of the chromatogram of FIG. 5 to the quantity of residue contained on an electronic assembly.

The various experiments showing the linearity depicted in FIG. 6 were performed with the reflow temperatures of three hundred ten degrees Centigrade with either air or nitrogen flowing. The rosin was applied to substrates in concentrations ranging from five percent to forty percent in alcohol. The relatively high reflow temperatures are required for lead rich solders, and such high temperatures have been found generally to increase the proportion of high molecular weight rosin oligomers which are detected by the GPC method. The invention is also applicable, however, to the lower reflow temperatures characteristic of eutectic solder alloy processes. The reactions which form the polymerized rosin are thermally induced and appear to be further complicated by the presence of oxygen, but our experiments show that the GPC technique is, nevertheless, effective in detecting such residue. Despite the complexity of the GPC chromatogram resulting from the complex and varied thermally induced chemical reactions of rosin, we have shown that it is convenient to determine the total concentration of rosin residues by GPC. The invention has the advantages of the conventional HPLC methods in that it is well suited for use in an assembly factory, but is more accurate than the conventional HPLC method which was shown to severely underestimate rosin concentration, and does not have the disadvantages associated with the various other methods.

The embodiment described is given for purposes of illustration only. Other modifications and embodiments may be made by those skilled in the art without departing from the spirit and scope of the invention. For example, in FIG. 1, solder paste may be used for solder elements 15, with rosin flux mixed into the solder paste, as is known in the art.

We claim:

1. A method for assembling electronic circuit devices comprising the steps of:
   forming a circuit including an array of first bonding pads on a substrate;
   forming solder elements over the first bonding pads;
   contacting the solder elements with an array of second bonding pads of an electronic device to be bonded to the substrate;
   heating the solder to a temperature sufficient to reflow such solder and to solder bond the first and second bonding pads, such bonding being in the presence of solder flux;
   cooling the solder to harden it, such cooling resulting in solder flux residue;
   subjecting the electronic circuit device to an extraction operation using an extraction solvent;
   analyzing the extraction solvent to determine the quantity of solder flux residue remaining on the circuit device; wherein the method is characterized by:
   using gel permeation chromatography to analyze the extraction solvent.

2. The method of claim 1 wherein:
   the substrate comprises a printed wiring board and is made of a material capable of absorbing liquid.

3. The method of claim 1 wherein:
   the extraction solvent is directed through at least one GPC column;
   light is directed through eluent exiting the GPC column;
   a chromatogram of the light transmitted through the eluent is made;
   and the area enclosed by the chromatogram is measured to determine rosin residue quantity.

4. The method of claim 1 wherein:
   prior to the extraction operation, the circuit device is subjected to a cleaning operation for removing a major part of the solder flux residue from the circuit device.

5. The method of claim 4 wherein:
   a succession of circuit devices are cleaned of solder flux residue through the use of a cleaning operation;
   only periodic ones of the succession of devices are subjected to the extraction operation;
   and the results of the analyzing step are used to adjust if necessary the cleaning operation on circuit devices that are cleaned subsequent to the analyzing step.

6. The method of claim 3 wherein:
   the GPC column contains porous cross-linked copolymers with different pore sizes.

7. The method of claim 6 wherein:
   the extraction solvent is directed successively through at least three GPC columns, each GPC column containing porous copolymers having different size pores with respect to pores in the other columns.

8. The method of claim 7 wherein:
   prior to the extraction operation, the circuit device is subjected to a cleaning operation for removing a major part of the solder flux residue from the circuit device.

9. The method of claim 8 wherein:
   a succession of circuit devices are cleaned of solder flux residue through the use of a cleaning operation;
   only periodic ones of the succession of devices are subjected to the extraction operation;
   and the results of the analyzing step are used to adjust if necessary the cleaning operation on circuit devices that are cleaned subsequent to the analyzing step.

* * * * *